United States Patent [19]

Farbood et al.

[11] Patent Number: 4,798,799

[45] Date of Patent: Jan. 17, 1989

[54] PROCESS FOR PRODUCING DIOL AND FURAN AND MICROORGANISM CAPABLE OF SAME

[75] Inventors: Mohamad I. Farbood, West Windsor; Brian J. Willis, Ramsey, both of N.J.

[73] Assignee: Fritzsche Dodge & Olcott Inc., New York, N.Y.

[21] Appl. No.: 903,858

[22] Filed: Aug. 29, 1986

Related U.S. Application Data

[63] Continuation of Ser. No. 513,270, Jul. 13, 1983, abandoned.

[51] Int. Cl.$^4$ .......................... C12N 1/14; C12P 7/18; C12P 17/04; C12R 1/645
[52] U.S. Cl. .................................... 435/254; 435/123; 435/126; 435/127; 435/132; 435/156; 435/158; 435/911

[58] Field of Search ............... 435/123, 126, 127, 132, 435/156, 158, 254, 255, 911

[56] References Cited

U.S. PATENT DOCUMENTS 3,880,712  4/1975  Moore ............................... 435/123
4,396,715  8/1983  Labows, Jr. ....................... 435/126

OTHER PUBLICATIONS

DeHoog, G. S. et al., *Antonie van Leeuwenhoek*, vol. 47, 1981, pp. 339–352.

Primary Examiner—Charles F. Warren
Assistant Examiner—Jeremy M. Jay
Attorney, Agent, or Firm—Cooper & Dunham

[57] ABSTRACT

The invention provides a microbiological method for preparing diol and furan compounds from a variety of substrates using the microorganism *Hyphozyma roseoniger*, CBS 214.83 and ATCC 20624.

12 Claims, No Drawings

PROCESS FOR PRODUCING DIOL AND FURAN AND MICROORGANISM CAPABLE OF SAME

This is a continuation of application Ser. No. 513,270, filed July 13, 1983 now abandoned.

BACKGROUND OF THE INVENTION

Dodecahyrdo-3a,6,6,9a-tetramethylnaphtho[2,1-b]furan (1) is an important fragrance chemical (see U.S. Pat. No. 3,029,255). It has been used in high quality perfume compositions and in functional products, such as fragrances for toiletries and household products, where a persistent amber effect is desired. Compound 1 is also a component of tincture of ambergris [see B. D. Mookherjee and R. R. Patel, Proceedings of the 7th International Congress of Essential Oils, Kyoto, Japan, (1977), paper number 136], and synthetic 1 has been used in artificial ambergris formulations. Compound 1 may be manufactured from 2-ethenyldecahydro-2-hydroxy-α-2,5,5,8a-pentamethyl-1-naphthalenepropanol (4), commonly referred to as Sclareol, obtained from Clary Sage (*Salvia Sclarea*).

U.S. Pat. No. 3,050,532 discloses a method of converting Compound 4 into dodecahydro-3a,6,6,9a-tetramethylnaphth[2,1-b]furan-2(1H)-one (2) using a two-stage oxidation sequence. In the first step an aqueous dispersion of Sclareol is intimately contacted with an alkali metal permanganate oxidizing agent, under alkaline conditions, to partially oxidize the Sclareol. During the second step the resulting aqueous reaction mixture from the first step is acidified and intimately contacted with a permanaganate or chromic acid oxidizing agent under acid conditions, thereby completing the oxidation.

Compound 2 may be readily converted to Compound 1 by known methods. For example, reducing Compound 2 with hydride reagents (see for example, Helv. Chim. Acta 1950, 33, 1308) provides decahydro-2-hydroxy-2,5,5,8a-tetramethylnaphthaleneethanol (3) which is readily converted by cyclization to Compound 1.

U.S. Pat. No. 3,029,255 discloses a method for making Compound 1 by dehydrating Compound 3 with Al$_2$O$_3$ at 200°–225° C., followed by heating in vacuo in the presence of β-naphthalene sulfonic acid (130° C. up to 160° C.) to effect cyclization to Compound 1.

Alternatively, Compound 1 may be obtained by cyclization of Compound 3 using toluene-p-sulfonyl chloride in pyridine, as disclosed by Cambie et al. (see Aust. J. Chem., 1971, 24, 591).

There is no teaching or suggestion in the prior art of converting labdane compounds via microbiological methods into decahydro-2-hydroxy-α,2,5,5,8a-tetramethylnaphthaleneethanol (3) or dodecahydro-3a,6,6,9a-tetramethylnaphtho[2,1-b]furan (1), according to the novel and commercially efficient process provided by this invention.

SUMMARY OF THE INVENTION

The present invention concerns a biologically pure culture of the microorganism *Hyphozyma roseoniger*, having the identifying characteristics of CBS 214.83 and ATCC 20624.

In another embodiment, the present invention concerns a culture containing the microorganism *Hyphozyma roseoniger*, having the identifying characteristics of CBS 214.83 and ATCC 20624, said culture being capable of producing a diol having the structure

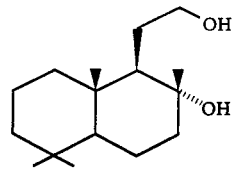

in a recoverable quantity upon the transformation of compounds from the group consisting of

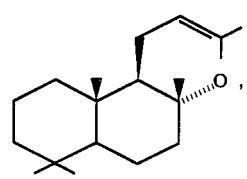

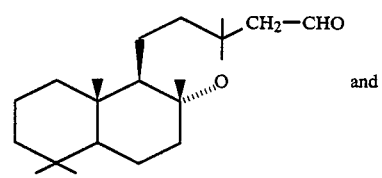

and

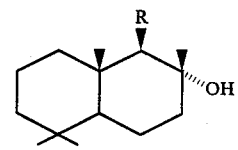

wherein R is

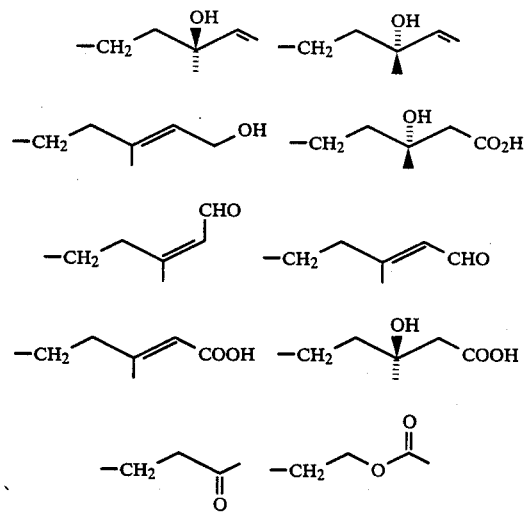

under aerobic conditions in an aqueous nutrient medium.

In still another embodiment, the present invention concerns a mixture prepared by cultivating the microorganism *Hyphozyma roseoniger*, having the identifying characteristics of CBS 214.83 and ATCC 20624, under aerobic conditions in an aqueous nutrient medium.

In a further embodiment, the present invention concerns a process for preparing a diol having the structure

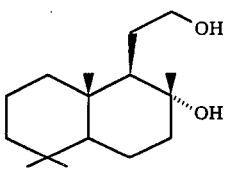

which comprises cultivating the microorganism *Hyphozyma roseoniger*, having the identifying characteristics of CBS 214.83 and ATCC 20624, under aerobic conditions in an aqueous nutrient medium containing one or more compounds from the group consisting of

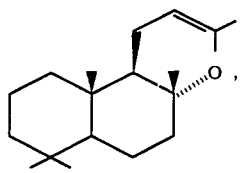

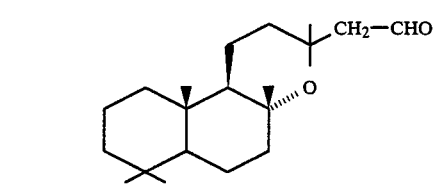

and

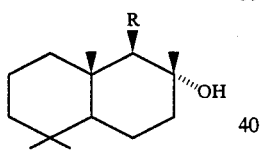

wherein R is

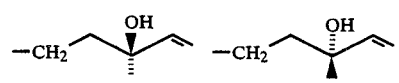

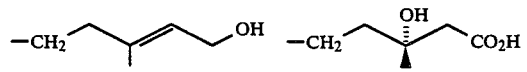

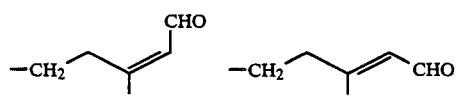

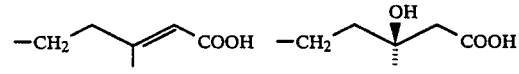

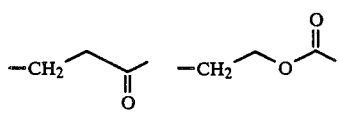

In a still further embodiment, the present invention concerns a process for preparing a furan compound having the structure

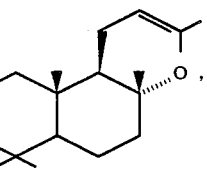

which comprises cultivating the microorganism *Hyphozyma roseoniger*, having the identifying characteristics of CBS 214.83 and ATCC 20624, under aerobic conditions in an aqueous nutrient medium containing one or more compounds from the group consisting of

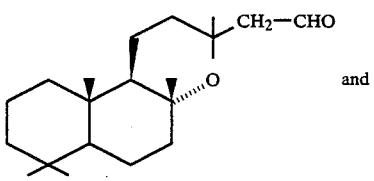

and

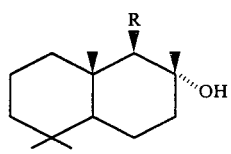

wherein R is

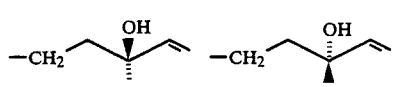

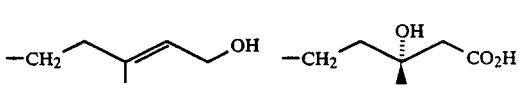

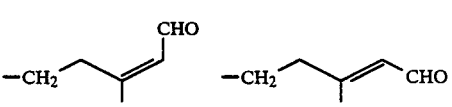

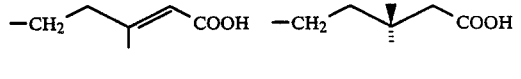

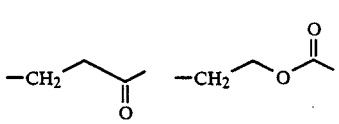

to form a diol having the structure

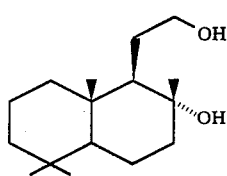
cyclizing the diol in the aqueous nutrient medium to form said furan compound; and recovering said furan compound.
BRIEF DESCRIPTION OF FIGURES
Figure 1 provides the structures of some of the compounds of interest in the present invention.
Figure 1
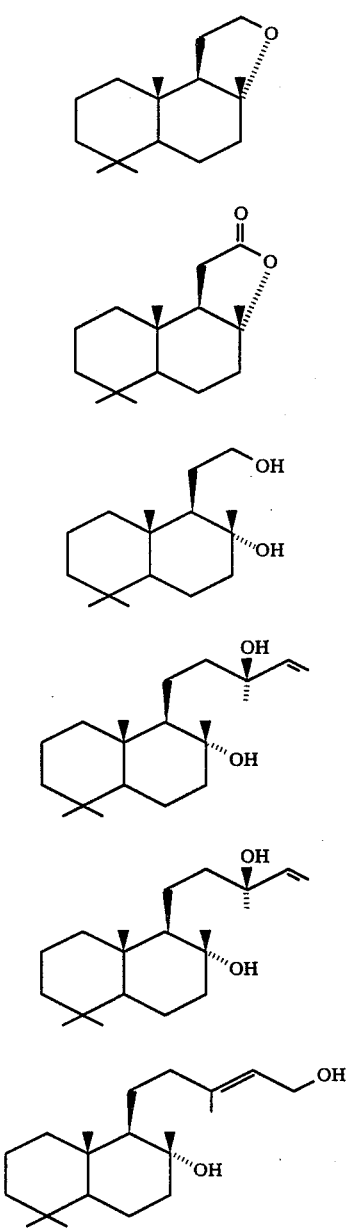
-continued
Figure 1
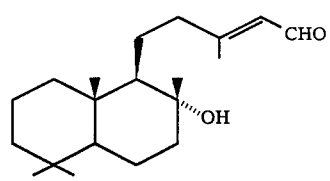
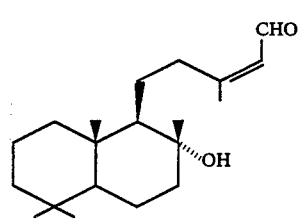
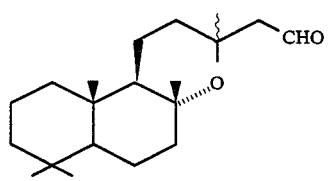
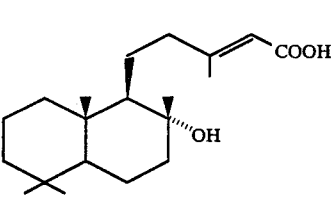
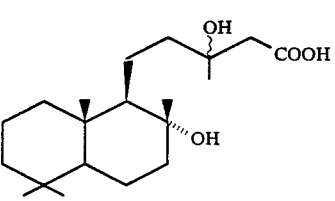
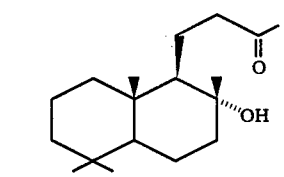
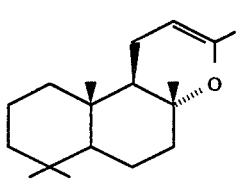
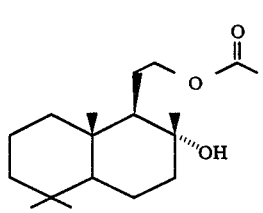
Compounds 4 through 14 may be used as substrates in the transformation process for the present invention to produce the desired products. Compounds 6, 11, and 13 have been observed as intermediates during the transformation of Sclareol according to the process of this invention. The transformation process involves cultivation of the microorganism Hyphozyma roseoniger, CBS 214.83 and ATCC 20624 in an aqueous nutrient medium in the presence of the compounds 4 through 14. These compounds may be used singularly or as a mixture containing any number of said compounds.

The form in which the microorganisms are used is not critical. They can be used as the culture (suspension), i.e. including the cells and the corresponding nutrient solution, or in the form of cells suspended in a buffer solution. The cells, or an enzyme extract thereof, may be immobilized on a suitable solid support, which may then be used to effect transformations.

The suspended culture mixture is prepared by inoculation of a suitable aqueous nutrient medium with the microorganism. A suitable nutrient medium is one which contains nitrogen sources, inorganic salts, growth factors, the desired substrate(s), and optionally other carbon sources. Some carbon sources suitable for use in the inventive process include, for example, glucose, galactose, L-sorbose, maltose, sucrose, cellobiose, trehalose, L-arabinose, L-rhamnose, ethanol, glycerol, L-erythrithol, D-mannitol, lactose, melibiose, raffinose, melezitose, starch, D-xylose, D-sorbitol, $\alpha$-methyl-D-glucoside, lactic acid, citric acid and succinic acid. Suitable nitrogen sources include, for example, nitrogen-containing organic substances such as peptone, meat extract, yeast extract, corn steep liquor, casein, urea, amino acids, or nitrogen-containing inorganic compounds such as nitrates, nitrites and inorganic ammonium salts. Suitable inorganic salts include, for example, phosphates of magnesium, potassium, calcium, or sodium. The above mentioned culture medium nutrients may be supplemented with, for example, one or more vitamins of the B group and/or one or more trace minerals such as Fe, Mo, Cu, Mn, and B, as desired. The Vitamins of trace minerals are not necessary when a small amount of yeast extract is added to the medium. Addition of an antibiotic, such as chloroamphinical or chlorotetracycline, may be desirable when bacterial contamination is a problem.

The cultivation of the microorganism may be carried out as a stationary culture or as a submersed (e.g., shaking culture, fermentor culture) under aerobic conditions. One may suitably work in the pH range of from between about 2.5 and about 9.0, and preferably in the range of from between about 3.0 and about 7.5 and most preferably between about 3.0 and about 6.5 The pH may be regulated by the addition of inorganic or organic acids, such as hydrochloric acid, acetic acid, and oxalic acid, or by the addition of bases, such as sodium hydroxide, and ammonium hyroxide, or by the addition of a buffer, such as phosphate or phthalate. The incubation temperature should suitably be maintained between about 12° C. and about 33° C., with a range between about 15° C. and about 30° C. being more preferred, and a range between about 18° C. and about 28° C. being most preferred.

The process in accordance with this invention may be conveniently carried out by adding one or more of the compounds 4 through 14 to the nutrient medium at the onset of cultivation, as the sole carbon source. Alternatively, the substrate may be added in combination with another carbon source, such as dextrose, either during cultivation, or when the carbon source is depleted. The only restriction on the concentration of substrate in the culture medium is that of being able to effectively aerate the culture. However, the substrate concentration is preferably in the range of between about 0.1 g/L and about 100 g/L, more preferably in the range of between about 0.5 g/L and about 50 g/L, and most preferably in the range between about 1.5 g/L about 30 g/L. The transformation can be suitably carried under any of the above mentioned conditions.

The total transformation time (after initial cultivation period) may vary depending on the composition of the nutrient medium and the substrate concentration. In general, shaking flask cultures require from between about 12 hours and about 264 hours. However, when a fermentor is used the cultivation time may be reduced to about 48 hours or less.

The transformation may be carried out using the cells of the microorganism isolated from the culture solution, or with an enzyme extract isolated from the cells in a manner well known to the art. In this case, the transformation can be conveniently carried out in a variety of aqueous nutrient mediums including, for example, in a buffer solution, in a physiological salt solution, in a fresh nutrient solution, or in water. The isolated cells or enzyme extract may be immobilized on a solid support and the desired transformation effected. Also, transformation of the substrate may be effected by mutants of this organism. Such mutants can be readily obtained by methods well known in the art, for example, by exposing the cells to UV or X-rays, or known mutagenic substances, such as for example, acridine orange.

The substrate can be added to the medium as a powder, or a slurry in an emulsifier such as Tween-80 (polyoxyethylenesorbitan monstearate), or as a solution in an emulsifier, or as a solution in a hydrophilic solvent such as acetone, methanol, ethanol, ethylene glycol, or dioxan. A surfac-active agent, or a dispersion agent can also be added to an aqueous suspension of the substrate, or the substrate can be emulsified using ultrasound.

Conventional antifoam agents, such as silicone oils (e.g., UCON), polyalkyleneglycol derivatives, maize oil, or soya oil, can be used to control foaming.

The transformation of the substrate can be monitored using standard analytical techniques such as GLC, TLC, HPLC, IR, and NMR. If a rapid disappearance of the substrate is observed more substrate can then be added, in order to maximize the transformation capacity of the microorganism. The process is generally terminated when most of the substrate has disappeared from the culture medium. Compound 3 may be recovered from the aqueous nutrient medium, or may be cyclized to the furan Compound 2, either in the aqueous nutrient medium, or after recovery. Isolation and purification of Compounds 1 or 3 from the fermentation broth may be achieved by conventional techniques including, filtration or centrifugation, solvent extraction, distillation, crystallization, and the like. Compound 3 may be converted to the furan Compound 1 by conventional cyclization methods well known in the art. For example, reaction of diol 3 with toluene-p-sulfonylchloride in pyridine at 0° C. according to the procedure described by Cambie et al. (see Aust. J. Chem., 1971, 24, 591), which is incorporated herein by reference. This procedure may optionally be employed either on the transformation mixture or on the recovered diol Compound 3. Examples of other cyclization methods are described by R. B. Wagner and H. D. Zook in "Synthetic Organic Chemistry", John Wiley, 1965, pp 838-839, which is incorporated herein by reference.

The microorganism employed in this invention was isolated from a soil sample obtained from central New Jersey, U.S. of America. This strain has been deposited with the Centraalbureau voor Schimmelculture and the American Type Culture Collection with the accession number CBS 214.83 and ATCC 20624, respectively.

The organism was studied and characterized by Centralbureau voor Schimmel Cultures (CBS). Due to the pink coloring of its colonies and its unique morphological and physiochemical properties, CBS has assigned the inventive microorganism the name *Hyphozyma roseoniger*.

This organism has distinct yeast and filamentous forms. Both forms exhibit similar biological properties and perform the transformations described herein.

The properties of the yeast phase of the said microorganism are described below:

1. Shape and Size

Growth on YM Agar: Pink, glistening, smooth colonies present filamentous growth cells are budding, round or cylindrical ca. 2×7 μm or sometimes larger.

Growth on Malt Extract Agar: Pink, occasionally brownish with formation of true hyphae after 2 to 3 weeks, with no clump connections, shiny.

Growth on Corn Meal Agar: Light orange-pink glistening. Smooth colonies fringed with mycelia.

Growth on Potato Dextrose Agar and Difco Malt Agar: Pink, smooth, glistening and occasionally turns black at room temperature after 2 to 3 weeks.

Growth on YPCA Agar: Attaining 8 mm diameter in 10 days, flat, slimy, pale orange (6A3; Kornerups Wanscher, 1978), with sharp, somewhat lobed margins.

Growth on ChA Agar: 4 mm diameter in 10 days. After 3 weeks centrally becoming olivaceous, with light brown (6D6) to dark brown (5F7), finally a submerged mycelium extending from the mucuous colony, leading to a dense, olive brown (4F4) colony locally with thin dirty, white central patches, later dense fascicles of aerial mycelium.

The organism produces true hyphae with anastomoses observed on potato and rice slides. It seems to be a hyphomycets fungus with a distinct yeast phase in its life cycle.

2. Fermentation on Sugars (see Table 1)

TABLE 1

| Compound | Fermentation | |
|---|---|---|
| | Gas | Acid |
| Glucose | − | − |
| Galactose | − | − |
| Maltose | − | − |
| Sucrose | − | − |
| Lactose | − | − |
| Raffinose | − | − |
| Melibiose | − | − |
| Inulin | − | − |

3. Assimilation of Carbon Compounds (see Table 2)

TABLE 2

| Assimilation of Carbon Compounds | | | |
|---|---|---|---|
| Glucose | + | Lactose | v |
| Galactose | + | Melibiose | + |
| L-sorbose | + | Raffinose | + |
| Maltose | + | Melezitose | + |
| Sucrose | + | Inulin | − |
| Cellobiose | + | Soluble starch | + |
| Trehalose | + | D-xylose | + |

TABLE 2-continued

| Assimilation of Carbon Compounds | | | |
|---|---|---|---|
| L-arabinose | + | D-sorbitol | + |
| D-arabinose | − | α-Methyl-D-glucoside | + |
| D-ribose | + | Salicin | − |
| L-rhamnose | + | Inositol | − |
| D-glucosamine | − | Lactic acid | + |
| Ethanol | + | Citric acid | + |
| Glycerol | + | Succinic acid | + |
| L-erythrithol | + | Glucono-γ-lactone | + |
| Adonitol | − | | |
| Ducitol | − | | |
| D-mannitol | + | | |

4. Splitting Arbutin: positive
5. Assimilaton of $NH_4NO_3$: positive
6. Assimilation of $KNO_3$: positive
7. Assimilation of $KNO_2$: positive
8. Growth on Ethylamine: positive
9. Growth on Vitamin-free Medium: positive
10. Growth at 12° C.: positive
11. Growth at 26° C.: positive
12. Growth at 30° C.: positive
13. Growth at 37° C.: negative
14. Growth at 45° C.: negative The properties of the filamentous form of the said organism are similar to the yeast phase with the following exceptions:

Growth on YM Agar: Pink, rough colonies, presents filamentous growth with true hyphae.

Growth on Malt Agar or Potato Dextrose Agar: Pink, rough colonies, presents filamentous growth after 2 weeks at room temperature, colonies turn black.

Growth on Potato and Rice Slides: Produces true hyphae with anastomoses.

Growth in Liquid Medium such as YM Broth: Pink, presents yeast-like growth and occasionally some mycellium.

Growth on Potato Sucrose Agar: Filamentous with evidence of a yeast phase.

The following examples serve to illustrate embodiments of the invention as it is now preferred to practice it but in no way are meant to limit the scope thereof. Unless otherwise stated, weights are in grams, temperatures are in degrees centigrade and pressure in mm Hg.

CL EXAMPLE 1

This example demonstrates the fermentation process using 2-ethenyldecahydro-2-hydroxy-α,2,5,5,8a-pentamethyl-1-naphthalenepropanol (4) as substrate.

Four flasks, each containing an aqueous solution (100 mL) of 0.1% $NH_4NO_3$, 0.1% $H_2KPO_4$, 0.05% $MgSO_4.7H_2O$, trace minerals, and Vitamin B complex were sterilized at 120° C. for 20 minutes. A 50% aqueous solution of dextrose (5 mL) and Tween-80 (0.1 mL), containing Sclareol (4) (10 mg) was added to each flask. Each flask was inoculated with 5% by volume of three days grown cells CBS 214.83 (ATCC 20624). The cultures were then incubated at 25±1° C. on a rotary shaker (200 rpm) for 3 to 4 days. After the initial incubation period a mixture of Sclareol dissolved in Tween-80 (8.0 g) was added in portions during the next 5 days, afterwhich the incubation was continued for a further 4 days. At the end of the incubation period the contents of the four flasks were combined, extracted with ethyl acetate (3×200 mL) and dried ($Na_2SO_4$). Evaporation of the solvent provided a crude extract (4.0 g), which was crystallized from hexane/chloroform to provide decahydro-2-hydroxy-2,5,5,8a-tetramethylnaphthaleneethanol (3) (2.4 g), mp 130.5°–131.5° C., (lit. 132°–133° C.) GLC purity 100%, H-NMR (CDCl3) δ0.79 (6H, 2s), 0.87 (3H, 2), (3H, 2), 0.9–20 (16H, m), 3.41–3.49 (1H, m), 3.72–3.79 (1H, m). IR (CHCl3) $\nu_{max}$, 3580, 3360, 2950, 1460, 1380 cm. MS m/e 236, 221, 117, 137, 109. $[\alpha]_{22}^{D} = -16.8°$ (CHCl3). [Literature 132°–133° C., $[\alpha]_D^{22.5} = -17.3°$ (CHCl3).] [See M. Stoll and M. Hinder Helv. Chim. Acta (1953) 36 1955–2008.]

EXAMPLE 2

This example demonstrates the efficacy of the fermentation process using different levels of Sclareol (4) as substrate.

A procedure similar to that described in Example 1 was used except that yeast extract (0.1 g) was substituted for the trace minerals and vitamins, and that the Sclareol (4) was recrystallized from hexanes, pulvarized, passed through a 50-mesh seive, and then mixed with an equal weight of Tween-80. After an initial incubation period of 4 days, the mixture of Sclareol (4) and Tween-80 was added to each flask incrementally over a period of 5 days and then incubated for an additional 4 days. Table 3 below shows the amount of Sclareol (4) added to each flask and the yield of isolated diol 3. Each product exhibited spectral data identical with that reported in Example 1.

TABLE 3

| Flask | Total Weight of Sclareol (4) g | Isolated Yield of Diol 3 % |
| --- | --- | --- |
| 1 | 2 | 81 |
| 2 | 3 | 74 |
| 3 | 5 | 71 |

EXAMPLE 3

This example demonstrates the efficacy of the fermentation process using resting cells (washed).

A procedure similar to that described in Example 1 was employed, except that after an initial incubation period of 3 days, the cells from 100 mL of culture broth were harvested and washed (3×25 mL) with 0.3×10$^{-4}$M phosphate buffer (pH=7.2) and separated by centrifugation. The washed cells were dispersed in the above mentioned buffer (100 mL) and incubated at 25±1° C. on a rotary shaker (rpm 200) for 7 days. Sclareol (0.5 g) dissolved in Tween-80 (5 g) was added incrementally to the suspension of cells during the first 4 days of incubation. At the end of the incubation period TLC monitoring indicated that all of the Sclareol (4) had been converted to the diol 3. Work-up, in the usual manner, provided diol 3 in 98% yield, and 99% GLC purity. The spectral data for this product was identical with that reported in Example 1.

EXAMPLE 4

This example demonstrates the fermentation process using each of Compounds 4 through 14 as substrates, to produce decahydro-2-hydroxy-2,5,5,8a-tetramethyl-naphthaleneethanol (3).

Eleven flasks, each containing an aqueous solution (100 mL) of medium described in Example 2 were sterilized at 120° C. for 20 minutes. A 50% aqueous solution of dextrose (4 mL), and Tween-80 (0.1 mL) containing 10 mg of corresponding substrate, was added to each flask. Each flask was then inoculated with 5% by volume of three days grown cells of CBS 214.83 (ATCC 20624) and the cultures were then incubated at 24±1° C. on a rotary shaker (200 rpm) for 3 days. After the initial incubation period, a mixture of substrate dissolved in Tween-80 (ratio 1:7 w/w) was added to each corresponding flask, after which the incubation was continued for several days (see Table 4). The progress of the transformations was monitored by TLC. At the end of the incubation periods, the contents of each flask were extracted with ethyl acetate (3×75 mL), the extracts dried (Na2SO4), and the solvent evaporated. The residues were separately purified by column chromatography on silica gel using hexane/isopropane (95/5) as solvent, and the yields of diol 3 were determined. Data for the eleven experiments are summarized in Table 4.

TABLE 4

Production of Compound 3 by CBS 214.83 (ATCC 20624) Using Different Substrates

| Substrate | (g/100 mL) | Total Incubation Time (days) | Yield of Diol 3 (%) |
| --- | --- | --- | --- |
| Compound 4 | 0.3 | 7 | 96 |
| Compound 5 | 0.3 | 11 | 89 |
| Compound 6 | 0.3 | 7 | 91 |
| Compound 7 | 0.2 | 10 | 51 |
| Compound 8 | 0.2 | 10 | 13 |
| Compound 9 | 0.2 | 10 | 7 |
| Compound 10 | 0.3 | 7 | 98 |
| Compound 11 | 0.3 | 6 | 100 |
| Compound 12 | 0.3 | 11 | 91 |
| Compound 13 | 0.24 | 8 | 98 |
| Compound 14 | 0.5 | 4 | 100 |

EXAMPLE 5

This example demonstrates a method for preparing Compounds 7, 8 and 9, which may be employed as substrates in the inventive process.

A solution of Sclareol (9.24 g, 0.03 mol) in methylene chloride (40 mL) was added in one portion to a mixture of pyridinium chlorochromate (12.93 g, 0.06 mol), sodium acetate (2.46 g, 0.03 mol), and methylene chloride (100 mL). The mixture was stirred for 4 h at 25° C. Ether (200 mL) was added and the supernatant decanted from the gummy precipitate. The precipitate was washed with ether (3×50 mL). The ethereal solution was passed through silica gel 60 (40 g) and the solvents evaporated.

The residue was dissolved in ethanol (2 mL) and ether (4 mL), and stirred at 25° C. with a solution of sodium bisulfite (15 g) in water (60 mL) for 3 h. The mixture was extracted with ether (2×30 mL). The aqueous layer was made basic with 10% sodium hydroxide and extracted with ether (4×50 mL). The ether extracts were dried (Na2SO4) and the solvent evaporated to yield 2.72 g of residue. Chromatography on silica gel 60 (70 g; eluant, hexane: ethyl acetate; 4:1) gave 0.74 g of trans-aldehyde 7, 0.69 g of cis-aldehyde 8, and 0.64 g of cyclic aldehydes 9. [(E)-1R-(1α,2β, 4aβ,-8aα)]-5-(decahydro-2-hydroxy-2,5,5,8a-tetramethyl-1-naphthalenyl)-3-methyl-2-pentenal (7) mp 83°–85° C., $[\alpha]_D$+14.2° (c, 5.76, CHCl3); $^1$H-NMR (CDCl3) δ0.78 (6H, s), 0.86 (3H, s), 1.17 (3H, s), 2.15 (3H, broad s), 0.8–2.5 (17H, m), 5.82 (1H, d, J=8 Hz), 9.98 (1H, d, J=8 Hz); IR (CHCl3) $\nu_{max}$ 3570, 3440, 2940, 2850, 1670, 1630, 1460, 1440, 1390 cm$^{-1}$; MS, m/e 306, 291, 273, 109, 95, 84; UV $\lambda_{max}$ (95% ethanol) 241 nm (calcd 231 nm) ($\epsilon$, 17,300). Anal. Calcd for C20H34O2: C, 78.37; H, 11.18. Found: C, 77.92, H, 11.02. [(Z)-1R-(1α,2β,4aβ,-8aα)]-5-(decahydro-2-hydroxy-2,5,5,8a-tetramethyl-1-naphthalenyl)-3-methyl-2-pentanal (8), mp 91°–93.5° C.

[α]$_D$+8.9 (c, 3.13, CHCl$_3$); $^1$H-NMR (CDCl$_3$) δ0.78 (6H, s) 0.87 (3H, s), 1.14 (3H, s), 1.98 (3H, broad s), 0.9–2.8 (17H, m), 5.75 (1H, d, J=8 Hz), 10.0 (1H, d, J=8 Hz); IR (CHCl$_3$) 3570, 3450, 2940, 2840, 1670, 1630, 1460, 1440, 1390 cm$^{-1}$; MS m/e 306, 273, 109, 95, 84; UV ν$_{max}$ (95% ethanol) 242 nm (calcd 231 nm) (ε, 13,000). Anal. Calcd for C$_{20}$H$_{34}$O$_2$: C, 78.37; H, 11.18. Found: C, 78.34; H, 11.02. [4aR-(4aα,6aβ,10bβ)]-dodecahydro-3,4a, 7,7,7,10a-pentamethyl-1H-naphtho[2,1-b]pyran-1-acetaldehyde (9), $^1$H-NMR (CDCl$_3$) δ0.78 (6H, s), 0.85 (3H, s), 1.25 (3H, s), 1.27 (3H, s). 0.9–2.6 (18H, m), 9.8–10.0 (1H, m); IR (film) ν$_{max}$ 2940, 2850, 1720, 1460, 1440, 1380, 1370 cm$^{-1}$; MS, m/e (two peaks of similar ms) 291, 273, 262, 245, 109, 43.

EXAMPLE 6

This example demonstrates a method for preparing Compound 10, which may be employed as a substrate in the invention process.

To a suspension of sodium hydride (0.72 g of 50% suspension, 0.015 mol; washed free of mineral oil with hexane) in dimethoxyethane (15 mL) was added a solution of ethyl diisopropylphosphonoacetate (3.78 g, 0.015 mol) in dimethoxyethane (30 mL) over a 10 min period. After hydrogen evolution has ceased, [1R-(1α,2β,4aβ,8a α)]-4-(2-acetyloxy-decahydro-2,5,5,8a-tetramethyl-1-naphthalenyl)-2-butanone (3.22 g, 0.01 mol, which may be prepared as described by J. A. Barltrop et al., in J. Chem. Soc., 1960, 4613) was added all at once. The mixture was heated at reflux for 21 h, then cooled and poured onto ice water (100 mL). The mixture was acidified with 6N hydrochloric acid, and extracted with hexane/ethyl acetate (4:1, 4×10 mL). The organic extracts were washed with water (2×10 mL), saturated sodium bicarbonate solution (2×15 mL), and dried (Na$_2$SO$_4$). The solvents were evaporated and the residue chromatographed (silica gel 60; eluant, hexane: ethyl acetate, 9:1) to provide 3.02 g of ethyl [(E,Z)-1R-(1α,2β,4aβ,8aα)]-5-(2-acetyloxy-decahydro-2,5,5,8a-tetramethyl-1-naphthalenyl)-3-methyl-2-pentenoate as a colorless viscous oil.

A mixture of ethyl [(E,Z)-1R-(1α,2β,4aβ,8aα)]-5-(2-acetyloxy-decahydro-2,5,5,8a-tetramethyl-1-naphthalenyl)-3-methyl-2-pentenoate (2.19 g, 0.00557 mol), isopropanol (65 mL), water (10 mL) and potassium hydroxide (1.47 g, 0.0223 mol) was heated at reflux for 24 h. The mixture was concentrated to 20 mL, water (50 mL) was added, and the mixture was extracted with ether. The aqueous phase was acidified with 6N HCl and extracted with ether (5×20 mL). The ether extracts were washed with brine, dried (Na$_2$SO$_4$), and the solvents evaporated to yield 1.781 g of crude product. Chromatography on silica gel 60 (eluant, hexane: isoproanol, 9:1) gave 0.455 g of the cis-isomer, and 1.223 g of the trans-isomer 10. Recrystallization from hexane/ethyl acetate yielded analytical samples [(Z)-1R-(1α,2β,4aβ,8aα)]-5-(decahydro-2-hydroxy-2,5,5,8a-tetramethyl-1-naphthalenyl)-3-methyl-2-pentenoic acid, mp 147°–149° C.; [α]$_D$ +62.96° (c, 4.66, CHCl$_3$); $^1$H-NMR (CDCl$_3$) δ0.81 (6H, s), 0.88 (3H, s), 1.21 (3H, s), 1.92 (3H, broad s), 0.9–2.4 (17H, m), 5.72 (1H, broad s), 6.8–7.3 (1H, v. broad s); IR (CHCl$_3$) ν$_{max}$ 3500, 3400, 2940, 2550, 1690, 1640, 1460, 1440 cm$^{-1}$; MS, m/e 322, 304, 289, 276, 109; UV λ$_{max}$ (95% EtOH) 228 nm (calcd 217 nm) (ε, 7300). Anal. Calcd for C$_{20}$H$_{34}$O$_3$: C, 74.49; H, 10.63. Found: C, 74.20; H, 10.40. [(E)-1R-(1α,2β,4aβ,8aα)]-5-(decahydro-2-hydroxy-2,5,5,8a-tetramethyl-1-naphthalenyl)-3-methyl-2-pentenoic acid, mp 151°–153° C. [α]$_D$ 9.44° (c, 4.83, CHCl$_3$); $^1$H-NMR (CDCl$_3$) δ0.79 (6H, s), 0.87 (3H, s), 1.15 (3H, s), 2.17 (3H, broad s) 0.9–2.4 (17H, m). 5.70 (1H, broad s), 5.8–6.1 (1H, broad s); IR (CHCl$_3$) ν$_{max}$ 3560, 3400, 2940, 2550, 1690, 1640, 1460, 1440 cm$^{-1}$; MS, m/e 322, 304, 289, 276, 109; UV λ$_{max}$ (95% EtOH) 230 nm (calcd 217 nm) (ε, 5700). Anal. Calcd for C$_{20}$H$_{34}$O$_3$: C, 74.49; H, 10.63. Found: C, 74.12; H, 10.52.

EXAMPLE 7

This example demonstrates a method for preparing Compound 11, which may be employed as a substrate in the inventive process.

To a solution of diisopropylamine (8.484 g, 0.84 mol) in tetrahydrofuran (90 mL) at 0° C. was added n-butyllithium (38.2 mL of a 2.2. M hexane solution, 0.084 mol) dropwise, over a 20 minute period. A solution of acetic acid (2.52 g, 0.042 mol) in tetrahydrofuran (20 mL) was added over a 15 minute period. The mixture was then heated at 50° C. for 45 minutes. The mixture was cooled to 25° C. and [1R-(1α,2β,4aβ,8aα)]-4-(2-acetyloxydecahydro-2,5,5,8a-tetramethyl-1-naphthalenyl)-2-butanone (4.508 g, 0.014 mol, which may be prepared as described by J. A. Barltrop et al., in J. Chem. Soc., 1960, 4613) in tetrahydrofuran (35 mL) was added over a 10 minute period. The mixture was stirred at 25° C. for 17 h and then heated at reflux for 30 minutes. The mixture was cooled to 25° C., afterwhich water (40 mL) and potassium hydroxide (5 g) were added. The mixture was heated at reflux for 4 h, then cooled, added to water (100 mL), and extracted with hexane/ethyl acetate (4:1) (3×30 mL). The aqueous layer was cooled to 0° C., acidified with 6N HCl, and extracted with hexane/ethyl acetate (4:1, 4×50 mL). The combined extracts were washed with brine, dried (Na$_2$SO$_4$), and then the solvent evaporated to yield 2.071 g of crude product. Chromatograph on silica gel 60 (eluant, hexane:ethyl acetate:acetic acid, (10:10:0.1) gave 1.434 g of acids 11. Crystallization from hexane/ethyl acetate gave an analytical sample, mp 136°–137.5° C., $^1$H-NMR (CDCl$_3$) δ0.76 (6H, s), 0.85 (3H, s), 1.16 and 1.19 (3H, 2s), 1.28 (3H, s), 0.8–1.9 (16H, m), 2.4–2.8 (2H, m), 6.1–6.6 (2H, broad s); IR (CHCl$_3$) ν$_{max}$ 3550, 2930, 2700, 1710, 1455, 1385 cm$^{-1}$; MS m/e 340, 304, 289, 109, 95, 43. Anal. Calcd for C$_{20}$H$_{36}$O$_4$: C, 70.54; H, 10.66. Found C, 70.99, H, 10.63.

EXAMPLE 8

This example demonstrates the conversion of α-ethenyldecahydro-2-hydroxy-α,2,5,5,8a-pentamethyl-1-naphthalenepropanol (4) to dodecahydro-3α,6,6,9a-tetramethylnaphtho[2,1-b]furan (1) using a two-step process.

A procedure similar to that described in Example 2 was used, except that seven flasks were used, and that the amount of Sclareol (4) added to each flask and the incubation period was varied (see Table 5). When incubation was complete the flasks were worked-up separately and seven samples of crude diol 3 obtained. Each sample was separately reacted with toluene-p-sulfonylchloride, in pyridine, according to the method of Cambie, et al., (see Aust. J. Chem., 1971, 24, 591) and each reaction product Kugelrohr distilled to provide furan 1. $^1$H-NMR (CDCl$_3$) δ0.83 (6H, 2s), 0.88 (3H, s), 0.9–1.8 (13H, m), 1.9–2.0 (1H, m), 3.77–3.92, (2H, m). IR (melt) ν$_{max}$ 2940, 1460, 1385, 1365 cm$^{-1}$, MS m/e 236, 221, 204, 177, 137, 97. Data for the seven experiments are sumarized in Table 5.

TABLE 5

| Wt. of Sclareol (4) | | Total Incubation | Product 1 | |
| --- | --- | --- | --- | --- |
| Flask | mg | Time (days) | *Yield (mg) | GLC Purity (%) |
| 1 | 160 | 7 | 115 | 95 |
| 2 | 240 | 8 | 169 | 97 |
| 3 | 320 | 9 | 220 | 97 |
| 4 | 400 | 10 | 270 | 93 |
| 5 | 400 | 14 | 258 | 96 |
| 6 | 560 | 14 | 361 | 97 |
| 7 | 720 | 14 | 468 | 97 |

*Yields do not take into account samples removed during monitoring.

EXAMPLE 9

This example demonstrates the direct cyclization of the transformation product decahydro-2-hydroxy-2,5,5,8a-tetramethylnaphthaleneethanol (3), without separation from the aqueous nutrient medium, to dodecahydro-3a,6,-6,9a-tetramethylnaphtho[2,1-b]furan (1).

A procedure similar to that described in Example 2 using Sclareol (2.0 g) as substrate in 100 mL of fermentation broth was employed. After 14 days total incubation time, the contents of the flask were transferred to a reaction vessel equipped for stirring and heating under reflux. Toluene-p-sulfonylchloride (2.48 g), sodium hydroxide pellets (25 g) and tetrahydrofuran (200 mL) were added and the mixture stirred at 20° C. After 5 h, additional toluene-p-sulfonylchloride (1.50 g) was added and the reaction mixture was stirred overnight. Next day the mixture was heated at reflux for 30 min, cooled, and extracted with ethyl acetate (3 × 100 mL). The combined extracts were dried ($Na_2SO_4$). The solvents were evaporated, and the residue Kugelrohr distilled to give 1.38 g of a solid, which by instrumental analysis contained 85% of dodecahydro-3a,6,6,9a-tetramethylnaphtho[2,1-b]furan (1).

EXAMPLE 10

This example demonstrates an alternative procedure for the direct cyclization of the transformation product decahydro-2-hydroxy-2,5,5,8a-tetramethylnaphthaleneethanol (3), without separation from the aqueous nutrient medium, to dodecahydro-3a,6,6,9a-tetramethylnaphtho[2,1-b]furan (1).

A procedure similar to that described in Example 2 using Sclareol (2.0 g) as substrate in 100 mL of fermentation broth was employed. After 14 days total incubation time, the contents of the flask were transferred to a reaction vessel equipped for stirring and heating under reflux. The fermentation broth was acidified with 6N hydrochloric acid (to about pH 1), ethyl acetate (100 mL) added, and the stirred mixture heated at reflux for 6 h. After cooling, the ethyl acetate layer was separated, washed to neutrality, and dried. The solvent was evaporated and the residue Kugelrohr distilled to give 1.4 g of a solid, which by instrumental analysis contained 38% of dodecahydro-3a,6,6,9a-tetramethylnaphtho[2,1-b]furan (1).

EXAMPLE 11

This example illustrates an alternative procedure for the direct cyclization of the transformation product decahydro-2-hydroxy-2,5,5,8a-tetramethylnaphthaleneethanol (3), without separation from the aqueous nutrient medium, to dodecahydro-3a,6,6,9a-tetramethylnaphtho[2,1-b]furan (1).

A procedure similar to that described in Example 8 was employed except that the ion exchange resin Dowex 50X2 400 (10 g) was added to the fermentation broth instead of 6N hydrochloric acid. Work-up, and Kugelrohr distillation, gave 1.32 g of a solid, which by instrumental analysis contained 37% of Compound 1.

The invention being thus described, it will be obvious that the same may be varied in many ways. Such variations are not to be regarded as a departure from the spirit and scope of the invention, and all such modifications are intended to be included within the scope of the following claims:

What is claimed is:

1. A biologically pure culture of the microorganism *Hyphozyma roseoniger*, deposit number ATCC 20624.

2. A biologically pure culture containing the microorganism *Hyphozyma roseoniger*, deposit number ATCC 20624, said culture being capable of producing a diol having the structure

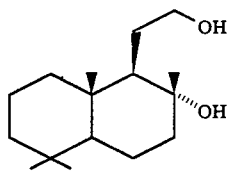

in a recoverable quantity upon the transformation of compounds selected from the group consisting of

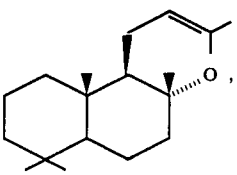

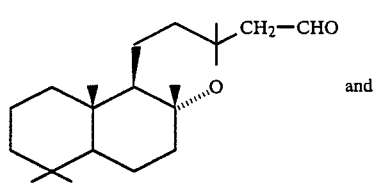

and

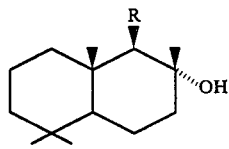

wherein R is

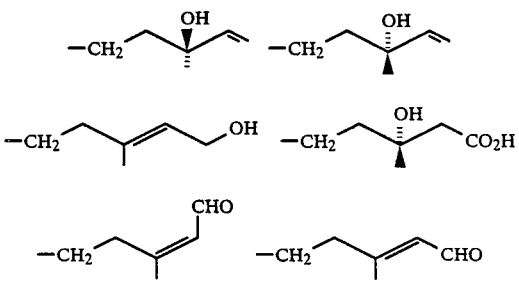

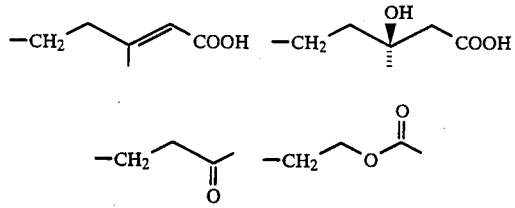

under aerobic conditions in an aqueous nutrient medium.

3. The culture of claim 1 in freeze-dried form.

4. A biologically pure mixture prepared by cultivating the microorganism *Hyphozyma roseoniger,* deposit number ATCC 2064, under aerobic conditions in an aqueous nutrient medium.

5. A biologically pure mixture prepared by cultivating the microorganism *Hyphozyma roseoniger,* deposit number ATCC 2064, to produce a diol having the structure

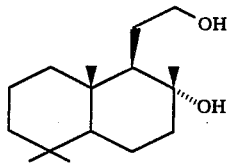

in a recoverable quantity upon transformation of compounds selected from the group consisting of

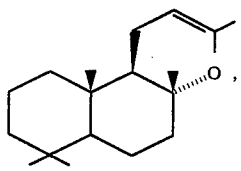

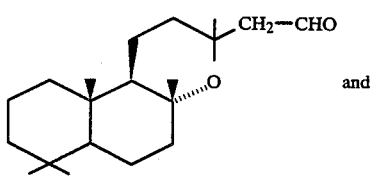

and

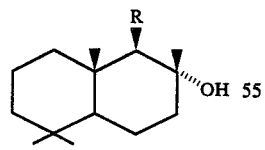

wherein R is

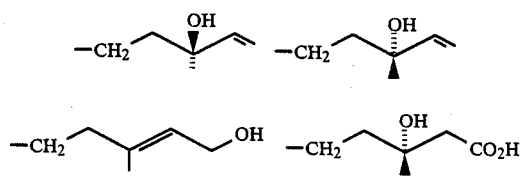

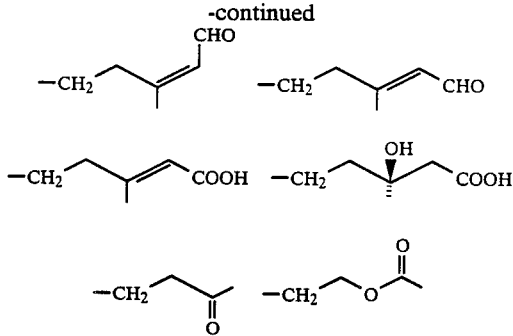

under aerobic conditions in an aqueous nutrient medium.

6. A biologically pure mixture prepared by cultivating the microorganism *Hyphozyma roseoniger,* deposit number ATCC 20624, to produce a diol having the structure

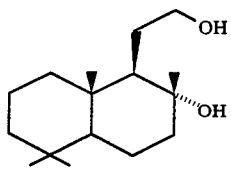

in a recoverable quantity upon transformation of compounds selected from the group consisting of

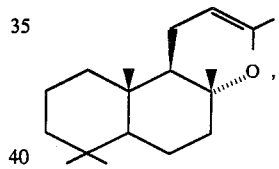

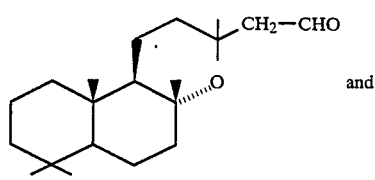

and

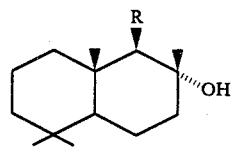

wherein R is

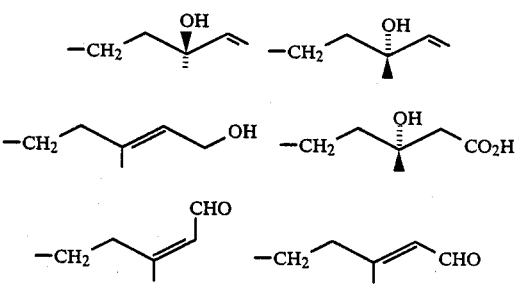

-continued

—CH₂—C(CH₃)=CH—COOH   —CH₂—CH(OH)—CH₂—COOH

—CH₂—CO—CH₃   —CH₂—CH₂—O—CO—CH₃ under aerobic conditions in an aqueous nutrient medium, wherein;
(i) the pH is between about 2.5 and about 9.0; and
(ii) the temperature is between about 12° C. and about 30° C.

7. A process for preparing a diol having the structure

[decalin structure with CH₂CH₂OH and OH substituents]

which comprises cultivating the microorganism *Hyphozyma roseoniger*, deposit number ATCC 20624, to produce said diol in a recoverable quantity upon the transformation of compounds selected from the group consisting of

[decalin-oxabicyclic structure with vinyl methyl group]

[decalin-oxabicyclic structure with CH₂—CHO side chain] and

[decalin structure with R and OH substituents]

wherein R is

—CH₂—CH(OH)—CH=CH₂    —CH₂—CH(OH)—CH=CH₂

—CH₂—C(CH₃)=CH—CH₂OH    —CH₂—CH(OH)—CH₂—CO₂H

—CH₂—C(CH₃)=CH—CHO    —CH₂—C(CH₃)=CH—CHO

-continued

—CH₂—C(CH₃)=CH—COOH   —CH₂—CH(OH)—CH₂—COOH

—CH₂—CO—CH₃   —CH₂—CH₂—O—CO—CH₃ under aerobic conditions in an aqueous nutrient medium, containing one or more compounds from said group and recovering said diol.

8. A process for preparing a diol having the structure

[decalin structure with CH₂CH₂OH and OH substituents]

which comprises cultivating the microorganism *Hyphozyma roseoniger*, deposit number ATCC 20624, to produce said diol in a recoverable quantity upon the transformation of compounds selected from the group consisting of

[decalin-oxabicyclic structure with vinyl methyl group]

[decalin-oxabicyclic structure with CH₂—CHO side chain] and

[decalin structure with R and OH substituents]

wherein R is

—CH₂—CH(OH)—CH=CH₂    —CH₂—CH(OH)—CH=CH₂

—CH₂—C(CH₃)=CH—CH₂OH    —CH₂—CH(OH)—CH₂—CO₂H

—CH₂—C(CH₃)=CH—CHO    —CH₂—C(CH₃)=CH—CHO

-continued

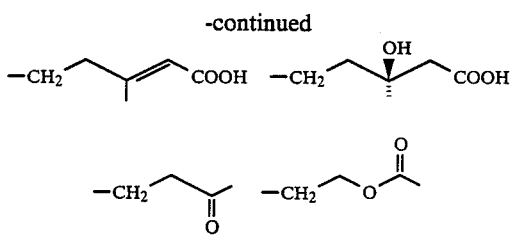

under aerobic conditions in an aqueous nutrient medium, containing one or more compound from said group; and recovering said diol.

9. A process for preparing a diol having the structure

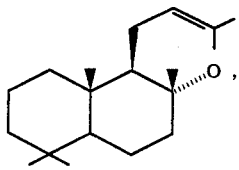

which comprises cultivating the microorganism *Hyphozyma roseoniger*, deposit number ATCC 20624, to produce said diol in a recoverable quantity upon the transformation of compounds selected from the group consisting of

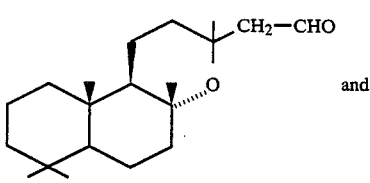

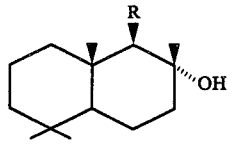

wherein R is

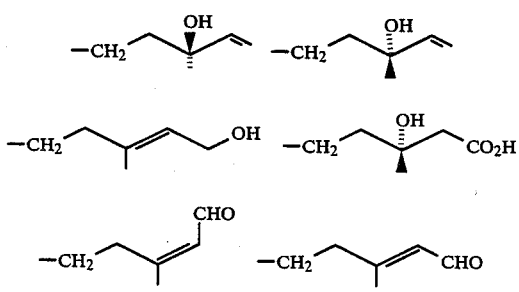

-continued

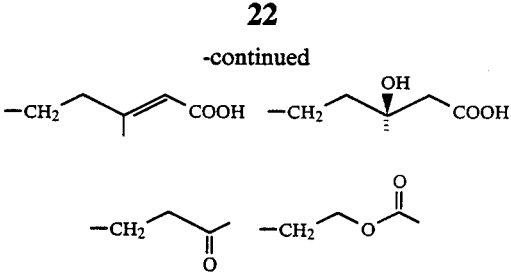

under aerobic conditions in a aqueous nutrient medium, containing one or more compounds from said group, wherein;
(i) the pH is between about 2.5 and about 9.0; and
(ii) the temperature is between about 12° C. and about 30° C. and recovering said diol.

10. A process for preparing a furan compound having the structure

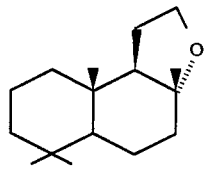

which comprises cultivating the microorganism *Hyphozyma roseoniger*, deposit number ATCC 20624, under aerobic conditions in an aqueous nutrient medium containing one or more compounds selected from the group consisting of

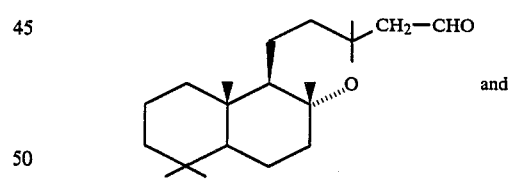

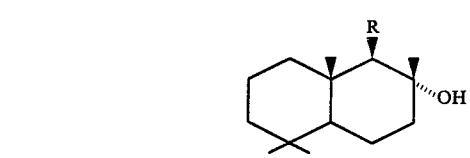

wherein R is

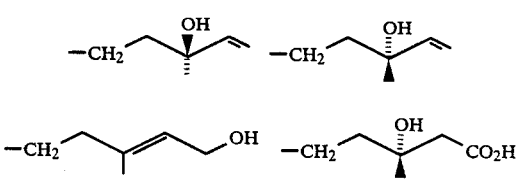

-continued

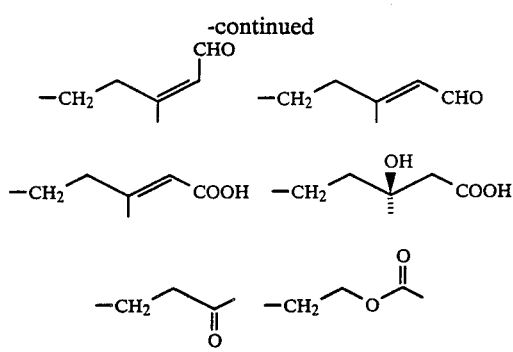

to form a diol having the structure

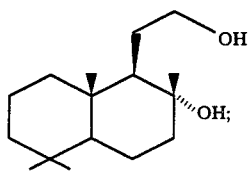

cyclizing the diol in the aqueous nutrient medium to form said furan compound; and recovering said furan compound.

11. A process for preparing a furan compound having the structure

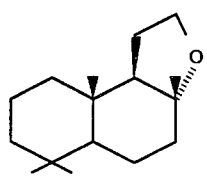

which comprises cultivating the microorganism *Hyphozyma roseoniger*, deposit number ATCC 20624, a diol have the structure

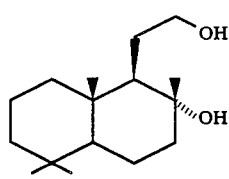

in a recoverable quantity upon the transformation of compounds selected from the group consisting of

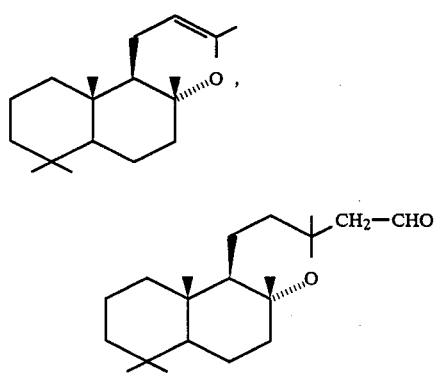

and

-continued

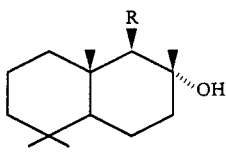

wherein R is

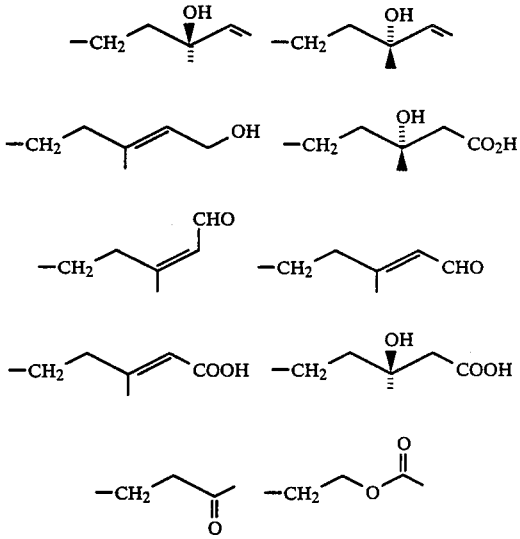

under aerobic conditions in an aqueous nutrient medium containing one or more compounds selected from said group to form said diol; adjusting the pH of the aqueous nutrient medium to between about 1 and about 3 to form said furan compound; and recovering said furan compound.

12. A process for preparing a furan compound having the structure

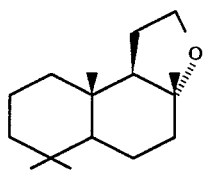

which comprises cultivating the microorganism *Hyphozyma roseoniger*, deposit number ATCC 20624, under aerobic conditions in an aqueous nutrient medium containing one or more compounds selected from the group consisting of

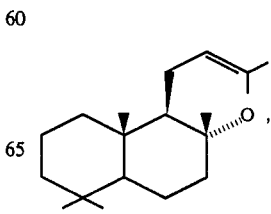

-continued
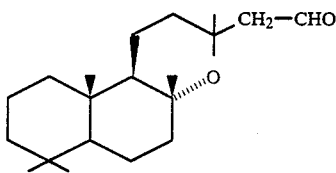
and
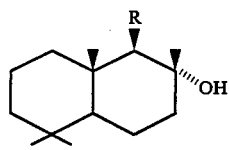
wherein R is
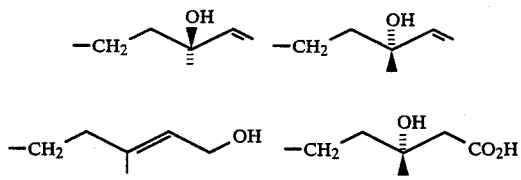
-continued
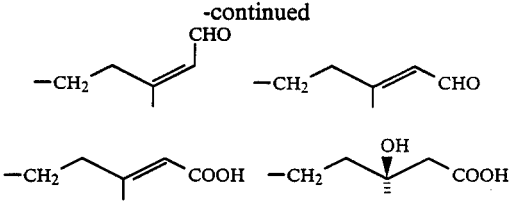
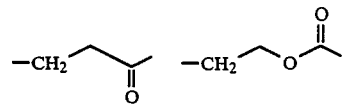
to form a diol having the structure
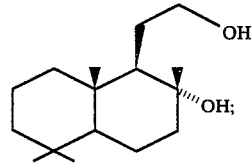
separating said diol; cyclizing said diol to form said furan compound; and recovering said furan compound.
* * * * *